US00PP26003P2

(12) United States Plant Patent
Barnett

(10) Patent No.: US PP26,003 P2
(45) Date of Patent: Oct. 20, 2015

(54) ***EUONYMUS* PLANT NAMED 'DANDEL'**

(50) Latin Name: *Euonymus fortunei*
Varietal Denomination: DANDEL

(71) Applicant: Daniel Barnett, Waterlooville (GB)

(72) Inventor: Daniel Barnett, Waterlooville (GB)

( * ) Notice: Subject to any disclaimer, the term of this patent is extended or adjusted under 35 U.S.C. 154(b) by 77 days.

(21) Appl. No.: 13/999,491

(22) Filed: Mar. 4, 2014

(51) Int. Cl.
*A01H 5/12* (2006.01)

(52) U.S. Cl.
USPC ..... Plt./246

(58) Field of Classification Search
USPC ..... Plt./246
See application file for complete search history.

*Primary Examiner* — Susan McCormick Ewoldt
(74) *Attorney, Agent, or Firm* — Penny J. Aguirre

(57) ABSTRACT

A new cultivar of *Euonymus*, 'DANDEL', that is characterized by its variegated foliage with broad creamy white margins and dark green and grey-green centers, its compact, upright and spreading plant habit with dense branching and stems with short internode lengths, and its slow growth habit.

2 Drawing Sheets

Botanical classification: *Euonymus fortunei.*
Variety denomination: 'DANDEL'.

BACKGROUND OF THE INVENTION

The present invention relates to a new and distinct cultivar of *Euonymus fortunei* and will be referred to hereafter by its cultivar name, 'DANDEL'. 'DANDEL' represents a new cultivar of evergreen shrub grown for use as an ornamental landscape plant.

The Inventor discovered the new cultivar in spring of 1993 as a naturally occurring branch mutation of *Euonymus* 'Emerald Beauty' (not patented) that was growing in a container at his nursery in Bordon, Hampshire, United Kingdom.

Asexual propagation of the new cultivar was first accomplished by the Inventor using softwood stem cuttings in 1994 in Eldon, Hampshire, United Kingdom. Asexual propagation by softwood cutting has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'DANDEL' as a unique cultivar of *Euonymus.*

1. 'DANDEL' exhibits variegated foliage with broad creamy white margins and dark green and grey-green centers.
2. 'DANDEL' exhibits a compact, upright and spreading plant habit with dense branching and stems with short internode lengths.
3. 'DANDEL' exhibits a slow growth habit.

The parent, 'Emerald Beauty', differs from 'DANDEL' in being less compact with stems with longer internode lengths and in having margins that are more yellow in color and narrower. 'DANDEL' can be most closely compared to other cultivars that have variegated foliage; 'Emerald Green' (not patented) and 'Emerald Gaiety' (not patented). 'Emerald Green' differs from 'DANDEL' in having green centers with golden margins and in being less compact. 'Emerald Gaiety' differs from 'DANDEL' in having much narrower white margins that are whiter in color.

BRIEF DESCRIPTION OF THE DRAWINGS

The accompanying colored photographs illustrate the overall appearance and distinct characteristics of a 2 year-old plant of the new cultivar as field grown (trimmed once) in Boskoop The Netherlands (and placed in a container for the photographs).

The photograph in FIG. 1 provides an overall view of the plant habit of 'DANDEL'.

Figure 1:
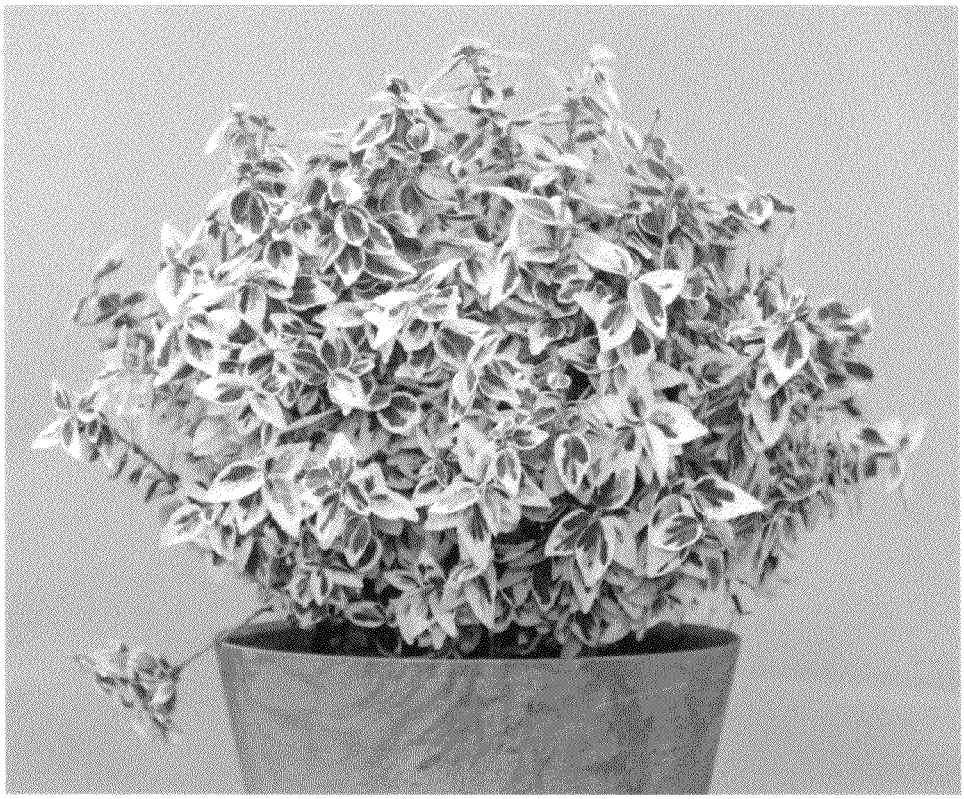
Figure 2:
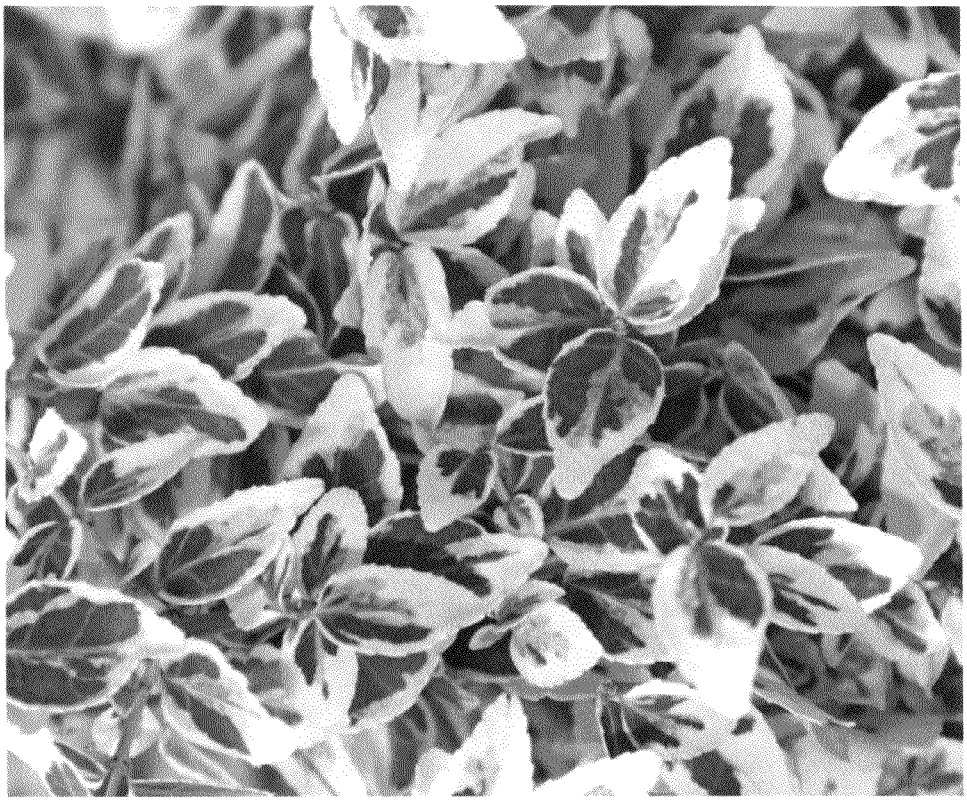

The photograph in FIG. 2 provides a close-up view of the foliage of 'DANDEL'.

The colors in the photographs may differ slightly from the color values cited in the detailed botanical description, which accurately describe the colors of the new *Euonymus.*

DETAILED BOTANICAL DESCRIPTION

The following is a detailed description of 2 year-old plants of the new cultivar as field grown in Boskoop, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Flowering has not been observed on the new cultivar.

*Plant type.*—Perennial evergreen shrub.

*Plant habit.*—Upright, dense, compact, spreading.

*Plant size.*—Reaches about 26.5 cm in height and 37.3 cm in width.

*Hardiness.*—At least hardy to U.S.D.A. Zone 6.

*Diseases and pests.*—Not susceptible or resistance to pests and diseases has been observed.

*Root description.*—Fibrous, moderately dense.

*Growth rate.*—Slow.

Stem description:

*Shape*.—Round.

*Stem color*.—Young: 192A to 192B, mature; 199B.

*Stem size*.—An average of 13 cm in length and 1.75 mm in diameter.

*Stem surface*.—Smooth and dull.

*Stem aspect*.—Upright.

*Stem strength*.—Strong.

*Branching*.—Dense basal branching, an average of 124 lateral branches.

Foliage description:

*Leaf shape*.—Ovate.

*Leaf division*.—Simple.

*Leaf base*.—Obtuse.

*Leaf apex*.—Obtusely acute to narrow obtuse.

*Leaf fragrance*.—None.

*Leaf venation*.—Pinnate, upper surface; 143B to 143C, lower surface; 146B.

*Leaf margins*.—Serrate.

*Leaf arrangement*.—Opposite.

*Leaf attachment*.—Petiolate.

*Leaf surface*.—Both surfaces smooth and dull.

*Leaf internode length*.—An average of 1.1 cm.

*Leaf size*.—An average of 2.7 cm in length and 1.7 cm in width.

*Leaf quantity*.—An average of 24 per stem (12 pairs).

*Leaf color*.—Young upper surface; N189A to N189B and 191A, broadly irregularly margin 8D, young lower surface; 191A to 191B, broadly irregularly margin 8D, mature upper surface; 147A and 189A, broadly irregularly margin with 155D and 158D, mature lower surface; 191A to 191B, broadly irregularly margin 8D.

*Petioles*.—About 3.5 mm in length and 1 mm in width, color; 137C, margins 193B to 193C.

*Stipules*.—None.

Inflorescence/fruit description: No flowers or fruit have been observed to date.

It is claimed:

1. A new and distinct cultivar of *Euonymus* plant named 'DANDEL' as herein illustrated and described.

* * * * *